United States Patent [19]

Lanciano

[11] Patent Number: 4,740,195
[45] Date of Patent: * Apr. 26, 1988

[54] DRAINAGE CATHETER

[75] Inventor: Andrew P. Lanciano, Framingham, Mass.

[73] Assignee: Medi-Tech, Incorporated, Watertown, Mass.

[*] Notice: The portion of the term of this patent subsequent to Feb. 17, 2004 has been disclaimed.

[21] Appl. No.: 9,240

[22] Filed: Jan. 30, 1987

Related U.S. Application Data

[63] Continuation-in-part of Ser. No. 829,764, Feb. 14, 1986, Pat. No. 4,643,720.

[51] Int. Cl.$^4$ ............................................. A61M 25/00
[52] U.S. Cl. ......................................... 604/95; 604/95; 128/657
[58] Field of Search ................... 604/95; 128/656–658, 128/4, 8, 772

[56] References Cited

U.S. PATENT DOCUMENTS

| | | | |
|---|---|---|---|
| 1,207,479 | 12/1916 | Bisgaard . | |
| 2,649,092 | 8/1953 | Wallace | 128/349 |
| 3,071,161 | 1/1963 | Ulrich | 138/120 |
| 3,294,633 | 12/1975 | Cook et al. | 128/349 |
| 4,203,430 | 5/1980 | Takahashi | 128/4 |
| 4,529,400 | 7/1985 | Scholten | 604/95 |
| 4,586,923 | 5/1986 | Gould et al. | 604/95 |

OTHER PUBLICATIONS

Gunther, R. W.; Dahmert, W.; "Self-Retaining Small-Looped Catheter for Narrow Bile Ducts in High Common Bile Duct Obstruction", Europ. J. Radiol 5 (1985).
"Angiomed Percutaneous Nephrostomy-Sets for the Loop Technique".
"Urological Special Procedure Sets & Devices", Van-Tec Incorporated (1985).
"Cope Loop Nephrostomy Catheter", U.S.C.I. Division, C. R. Bard Inc., (product literature).

Primary Examiner—Stephen C. Pellegrino

[57] ABSTRACT

A medical device of improved design includes an elongated member for insertion into the body, a flexible tension member extending along the elongated member to an attachment upon which tension is desired to be applied, and locking means associated with the elongated member at a point outside of the body to secure said flexible member under tension. The locking means consists of a pair of locking members disposed in close association with each other at a predetermined point along the proximal portion of said flexible tension member, one locking member being movable relative to the other locking member in motion laterally across the path of the tension member under tension to a locking position in which the tension member is bent and secured between cooperating locking members. Preferably, one locking member is rotatable relative to the other. The flexible tension member may extend within a fluid-carrying conduit defined by the elongated member, which in preferred embodiments is in the form of a catheter.

12 Claims, 1 Drawing Sheet

U.S. Patent
Apr. 26, 1988
4,740,195
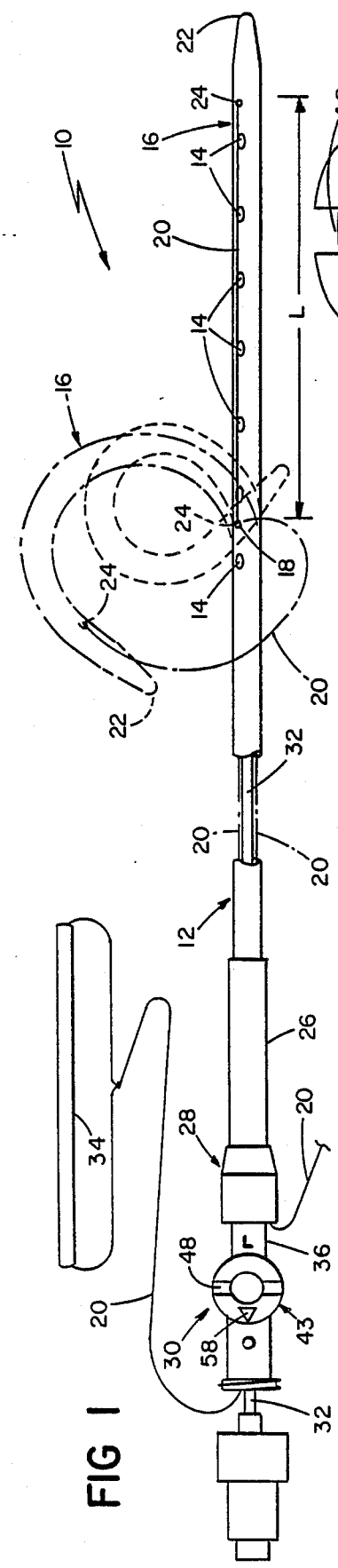
FIG 1
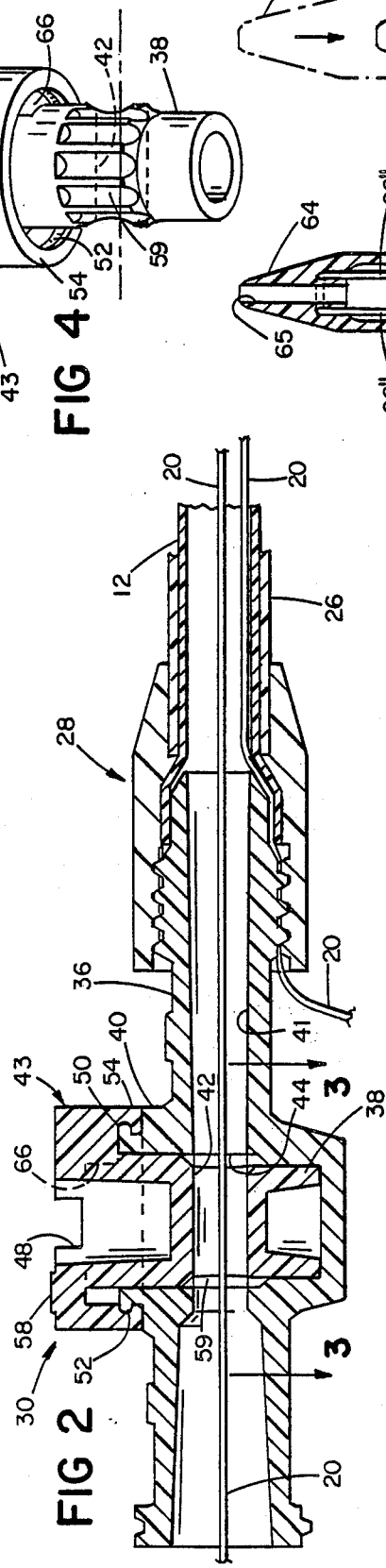
FIG 2
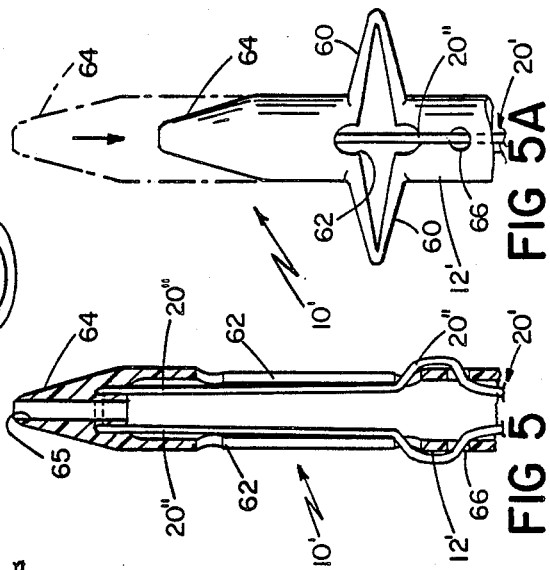
FIG 4
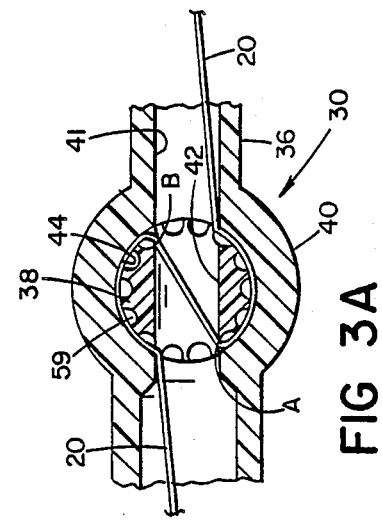
FIG 5
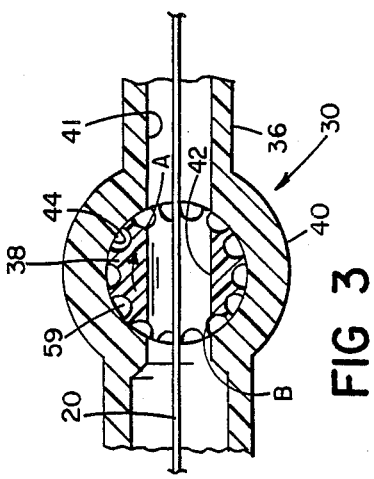
FIG 5A
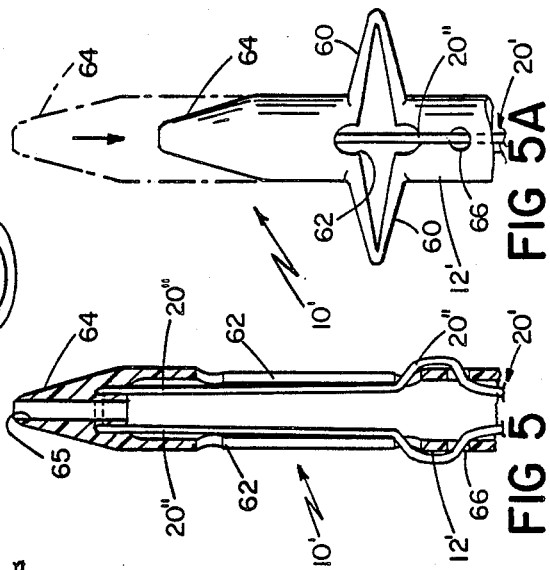
FIG 3
FIG 3A

DRAINAGE CATHETER

BACKGROUND OF THE INVENTION

This application is a continuation-in-part of U.S. Ser. No. 829,764, filed Feb. 14, 1986, now U.S. Pat. No. 4,643,720 issued Feb. 17, 1987.

The invention relates generally to catheters.

Kidney catheterization and suprapubic catherization of the bladder are used to drain the kidney or bladder after surgery or when the genito-urinary system is blocked by an obstruction. Catheters designed for this technique are inserted percutaneously by first piercing the lower abdominal wall with a large hypodermic needle, fitting a cannula over the needle and then placing the catheter within the bladder. These catheters are also used to drain abscesses, other sites of fluid collection, and other viscera such as the stomach and biliary system.

Bisgaard U.S. Pat. No. 1,207,479 describes a catheter with a so-called pigtail loop at its distal end which both ensures drainage of the bladder and prevents accidental removal of the catheter. The pigtail loop is tightened by pulling on the proximal end of a flexible tension member which extends through the catheter. The proximal end of this member is held in place by axially placing a hollow cap into or over the proximal end of the catheter tube, thus trapping the flexible tension member, the protruding end of which can then be cut. An alternative technique is described by Cook et al. U.S. Pat. No. 3,924,677 where the flexible tension member is trapped between two or more hollow tubes, one of which is slidably inserted axially into the other. A short length of the flexible tension member is generally left hanging from the catheter tube so that if the tension member becomes loose it can be retightened.

Wallace, U.S. Pat. No. 2,649,092 describes a catheter with lateral wings at the distal end for providing draining and preventing accidental removal. The wings are extended by pulling a flexible member proximally to retract the distal tip end.

SUMMARY OF THE INVENTION

The invention relates to a medical device comprising an elongated member for insertion into the body, a flexible tension member extending along the elongated member to an attachment upon which tension is desired to be applied, and locking means associated with the elongated member at a point outside of the body to secure the flexible member under tension.

According to the invention, the locking means comprises a pair of locking members disposed in close association with each other at a predetermined point along the proximal portion of the flexible tension member, one locking member being movable relative to the other locking member in motion laterally across the path of the tension member under tension to a locking position in which the tension member is bent and secured between cooperating locking members.

In preferred embodiments, one of the locking members rotates relative to the other, effectively jamming the tension member therebetween, and, preferably, the rotatable member has an aperture therethrough having an axis aligned with the direction of extent of the tension member, the tension member extending from the attachment, along the elongated member, through the aperture, to a proximal region where tension is applied to the tension member, rotation of the rotatable member serving to form multiple bends in the tension member. The elongated member comprises a hollow flexible tube and the flexible member extends within the tube, and, in locking position, the locking members are disposed in non-obstructing relationship to fluid passage through the tube, preferably the elongated member is a catheter, more preferably, the catheter has proximal and distal ends, and defines an opening near but spaced from the distal end, and the flexible tension member is attached to the distal end of the catheter and passes from the outside, through the opening, whereby, when the flexible member is tensioned, the distal end of the catheter is drawn toward the opening forming a loop in the distal end portion of the catheter. Still more preferably, the flexible tension member extends from the outside, through a second opening in the catheter relatively nearer the distal end and passes within the catheter toward the proximal end to a point of securement. The pair of locking members comprises mated rotatable and stationary members, the rotatable member having an aperture alignable with the passage of the tube, the flexible tension member passing freely through the aperture, the rotating member adapted to be rotated within the stationary member and thereby trap the flexible tension member between the rotatable and stationary members while still permitting liquid to flow in the tube. Preferably the rotatable member and stationary member are of the general form of a stopcock.

According to another aspect of the invention, a method of fixing the elongated member described above within a body cavity comprises inserting the distal end of the member into the body cavity, pulling the proximal end of the flexible tension member and thereby causing the distal end of the elongated member to form, within the body cavity, into a shape capable of resisting displacement from the body cavity, and moving one locking member laterally across the path of the flexible tension member to secure it.

In the preferred embodiment of this aspect of the invention, the method comprises rotating one locking member relative to the other, effectively jamming the flexible tension member therebetween, and the elongated member is in the form of a catheter having proximal and distal ends and defining a conduit for flow of fluid therewithin, and the method comprises securing the flexible tension member in a manner still permitting flow of fluid from the distal end to the proximal end of the catheter, and attaching a conduit-forming member to the proximal end of the catheter whereby the flexible tension member is positioned within the conduit-forming member.

Other features and advantages of the invention will be understood from the following description of a presently preferred embodiment, and from the claims.

DESCRIPTION OF THE PREFERRED EMBODIMENTS

The drawings will first briefly be described.

Drawings

FIG. 1 is a diagrammatic representation of a catheter embodying the invention;

FIG. 2 is a sectional representation of rotational and fixed locking members at the proximal end of the catheter;

FIGS. 3 and 3a are cross-sectional views of the rotational member of the locking device in its open and locked positions, respectively;

FIG. 4 is a perspective view of the rotating member of the locking device; and

FIG. 5 is a side section view of the distal end portion of an alternate embodiment of a catheter employing the invention, while FIG. 5a is a side view of the distal end portion of the catheter of FIG. 5 taken at 90°, with the flexible member under tension.

Structure

Referring to FIG. 1, catheter 10 comprises a hollow flexible tube 12 having a distal portion of length, L, e.g., 3 inches (7.5 cms) which is preformed to approximate a circular arc. In the wall of this portion are formed a series of drainage holes 14 of 2 mm diameter, arranged to lie facing inwardly of the arc. A flexible tension member 20 extends from a rod 34 outside the proximal end of the catheter, through the catheter to hole 18 lying slightly proximal of the series of drainage holes 14. The flexible member emerges to the outside through this hole 18. It re-enters the tube through a further hole 24, located distally of the series of holes 14, and is effectively anchored to the catheter tube by passing back along the inside of the catheter to the proximal end of catheter 12 where it is held between adapter 28 and threaded axial portion 36 of locking device 30. Axial portion 36 and adapter 28 are secured together by mating screw threads and cyanoacrylate adhesive. Flexible member 20 extends along these mating threads and is thus mechanically secured in place.

When catheter 10 is to be placed inside the body cavity, rigid, elongated cannula 32 is placed within catheter 10 and passes from its distal to its proximal end so that catheter 10 lies in a straight line, as shown in FIG. 1. Cannula 32 is made of a tubular metal rod which fits snugly into catheter 10. When the catheter is in position in the body, cannula 32 is removed and the distal end of catheter 10 will form a pigtail loop, as shown by dotted lines in FIG. 1. When flexible tension member 20 is pulled from its proximal end, holes 18 and 24 are drawn closely together and the intervening portion of the catheter tube is held in a tighter "pigtail" loop as shown in dashed lines in FIG. 1. This loop prevents removal of the catheter once it is inserted into a body cavity, and, by facing inwardly, the drainage holes 14 are protected from being blocked by structures in the body. At the extreme distal end of catheter 10 is hole 22 which represents the distal end of a continuous passage 41, of inner diameter between 1 and 2 mm, which allows insertion of catheter 10 into the body cavity over a guidewire, using tubular cannula 32. This passage also enables drainage of fluid from the distal to proximal end of the catheter when the guidewire is removed. Catheter 10 is preferably formed of biocompatible resin provided in a selected length from about 15 to 30 cm and sized from about 6 to 14 French in diameter. The distal loop is preformed by heating the catheter with hot water at approximately 75° C. for 30 to 45 seconds over a curved mandrel. The catheter will thus assume the shape of the mandrel in its resting position, but the flexible tension member is needed to hold the loop form securely.

At the proximal end of tube 12 is a short, larger diameter hollow tube 26 which is heat shrunk onto tube 12. This assembly is secured, by cyanoacrylate adhesive, to hollow adaptor 28, which in turn is secured to tension member locking device 30. Flexible member 20 passes through all these components and, outside of the catheter, forms a loop through hollow rod 34.

Referring also to FIG. 2, locking device 30 includes: fixed axial portion 36, which is secured to catheter tube 12 via tube 26 and adapter 28; fixed, external housing portion 40, which defines a receiving bore perpendicular to axial portion 36; and rotatable member 38 inside of housing 40. Rotatable member 38 is tightly fitted to the bore of housing 40 and engages upon housing 40 by snap fit of ridge 50, about the rim of the housing, within groove 52 formed about the inner surface of overhanging lip 54. Member 38 has a cross bore 42 having a first aligned position (FIG. 3) in which it forms a part of a continuous passage 41 running from the distal end to the proximal end of catheter 10, through which tension member 20 extends. When rotating member 38 is turned 180° from this first aligned position (FIG. 3a), it is again aligned and forms a part of continuous passage 41 through which fluid can flow. (Indicator 58 on the top surface of member 38 (FIG. 4) is in alignment with the axis of the catheter when the continuous passage 41 is open.) The locking member parts are suitably formed as by molding from structural plastic, e.g., nylon or Delrin TM. Indeed, it is possible to employ a standard stopcock to form the locking device as shown in FIG. 1. In the embodiment shown, the handle of the stopcock has been removed and an actuating groove 48 has been formed in its place. Alternatively, the stopcock can be used without modification with perhaps some other provision to prevent rotating member 38 from being inadvertently dislodged to a nonaligned or unlocked position.

Referring to FIGS. 3 and 3a, the locking action of rotating member 38 is shown schematically. Space 44 between housing member 40 and rotating member 38 is exaggerated for clarity, the clearance between the outer surface of housing 40 and opposed surface of rotating member 38 being less than the thickness of flexible member 20, and the surface of member 38 about cross bore 42 defines longitudinal flutes 59 which allow reduced friction while securing tension member 20. (In the case of use of a stopcock formed of self-lubricating structural resin, a running fit between the opposed surfaces of member 38 and housing 40 of as little as one or a few thousandths of an inch (0.25 mm or more) may be employed.)

In the first aligned position (FIG. 3), the flexible member, which may be a thin string-like member, e.g., of surgical suture material, extends freely through cross bore 42 of rotating member 38. Referring to FIG. 3a, rotating member has been rotated 180° to a realigned position such that continuous passage 41 is not interrupted. By this rotation, flexible member 20 has been trapped between the rotating member 38 and the wall defining the bore of housing 40, and twisted into an "S" configuration. This can effectively lock the tension member in position after it has been tensioned by the desired amount. The tension member can be unlocked by returning the rotating member to its initial position by turning in the opposite direction. Rod 34, or other suitable tool, can be used to turn rotating member 30 by inserting it into groove 48 and turning.

Locking, according to the invention, results from the basic action of a locking member that passes laterally across the path of the flexible tension member, when under tension, to a second stable position, relative to a stationary locking part.

This motion enables a number of locking effects which, in the preferred embodiment, are combined to achieve a very secure lock on the flexible tension member in a simple and inexpensive manner.

First, there is a so-called knotting effect that is achieved by the simple tight contortion of the flexible member about a movable member that has moved laterally across the tension member path.

Second, there is a wedging effect dependent upon the resilience of the flexible tension member, and the relatively close clearance between opposed surfaces of the movable and fixed locking parts.

Third, there is enhancement of the wedging effect attributable to slight resilience of the moving and fixed parts themselves, further enhanced by the flutes 59, when the tension member is wedged between them, as can be achieved when structural plastic parts are employed. Note that slight resilience of the locking parts enables them to fit more closely together and thus inhibit leakage to the outside.

Fourth, there is a doubling up action made possible by use of rotation to achieve the lateral motion of the locking member across the tension member path. As can be seen in FIGS. 3 and 3a, all of the above-mentioned effects can be achieved at two different regions A and B when rotation of the rotatable member occurs in the direction of the arrow in FIG. 3.

Fifth, because of close-fit of the parts, the locked position of the locking member is frictionally secured.

All of these effects can be uniquely achieved by use of the stopcock configuration mentioned above, and as shown in the drawings.

Referring to FIG. 4, the movable member 38 is generally of rod form having cross-bore 42. Portions of the rod extending to both sides of cross-bore 42 are shaped to mate closely with correspondingly shaped bearing surfaces of the stationary housing part. At least in the region of the exposed end 43 of the rod, the surfaces fit with sufficient tightness to prevent leakage to the outside.

Also, the aggregate friction of the mating parts is sufficient to enable the parts to remain securely in the position selected when twisting the member.

Use

Standard techniques are used to insert the distal tip of catheter 10 into a patient. Since the catheter is of fluoroscopically dense material, its progress into the body is readily observed. Briefly, these techniques involve the placement of a guidewire into the body cavity, the insertion of a stiff cannula 32 into catheter 10, such that loop 16 is straightened (solid line in FIG. 1) and advancement of cannula and catheter over the guidewire. Once in position, with all the holes inside the body cavity to be drained, the cannula can be removed. The pigtail may be formed by removing the guidewire and gently pulling on the proximal end of flexible member 20. Flexible member 20 is then locked in place by turning rotating member 38 by 180°, e.g., by inserting rod 34 or other tool into groove 48 and turning it. Indicator 58 is provided adjacent groove 48 on the housing to show locked and unlocked positions so that the physician can readily determine which way the rotating rod should be turned. A stop 66, beneath the lip 54 of rotatable member 38, is provided to engage upon a corresponding shoulder of housing 40 (not shown) to prevent wrong rotation of member 38. Once locked, flexible member 20 can be cut to leave a short projection from the proximal end of catheter 10, a drainage tube can be connected to member 30, with the proximal end of flexible member 20 inserted into the drainage tube. This set-up will prevent liquid from passing along flexible member 20 and out of the path of continuous tube 44 as has been a problem with prior devices in which the tension member extends to the outside and leakage occurs by wicking action.

To remove the catheter, the drainage tube is disconnected, the short proximal length of flexible member 20 exposed, rotating member 38 is turned 180° back to its original position, and the catheter pulled gently out.

Other embodiments are within the following claims. For example, the locking device of the invention may be employed for securing a flexible tension member associated with elongated medical devices of other form. For example, referring to FIGS. 5 and 5a, the distal end portion of drainage catheter 10' having elongated hollow portion 12' defines wing members 60 formed by longitudinal slits 62 in the catheter wall. Flexible tension member 20' extends in a loop within the catheter to fixation by fusing at the distal tip 64, about axial opening 65, provided for introduction of the catheter along a guidewire. The two segments 20" of the flexible tension member extend from the distal tip, out through slits 62, back into the catheter via holes 66 and then together along within the catheter, through the crossbore 42 of movable member 38. The segments 20" are drawn proximally, e.g, by turning the rotatable member 38, and secured by the locking device of the invention, as described above, with wings 60 projecting laterally and secured to prevent accidental dislodgement of the catheter.

What is claimed is:

1. A medical device comprising an elongated member for insertion into the body, a flexible tension member extending along said elongated member to an attachment upon which tension is desired to be applied, and locking means associated with the elongated member at a point outside of the body to secure said flexible member under tension, THE IMPROVEMENT WHEREIN
said locking means comprises a pair of locking members disposed in close association with each other at a predetermined point along the proximal portion of said flexible tension member, one said locking member being movable relative to the other said locking member in motion laterally across the path of said tension member under tension to a locking position in which the tension member is bent and secured between said cooperating locking members.

2. The medical device of claim 1 in which one of said locking members rotates relative to the other, effectively jamming said tension member therebetween.

3. The medical device of claim 2 in which said rotatable member has an aperture therethrough having an axis aligned with the direction of extent of said tension member, said tension member extending from said attachment, along said elongated member, through said aperture, to a proximal region where tension is applied to said tension member, rotation of said rotatable member serving to form multiple bends in said tension member.

4. The medical device of claim 1, 2 or 3 wherein said elongated member comprises a hollow flexible tube and said flexible member extends within said tube, and in said locking position, said locking members are disposed in non-obstructing relationship to fluid passage through said tube.

5. The medical device of claim 4 in the form of a catheter.

6. The medical device of claim 5 wherein said catheter has proximal and distal ends, and defines an opening near but spaced from said distal end, and said flexible tension member is attached to the distal end of said catheter and passes from the outside, through said opening, whereby, when said flexible member is tensioned, the distal end of the catheter is drawn toward said opening forming a loop in the distal end portion of said catheter.

7. The medical device of claim 6 wherein said flexible tension member extends from the outside, through a second opening in said catheter relatively nearer the distal end and passes within said catheter toward the proximal end to a point of securement.

8. The medical device of claim 2 or 3 wherein said pair of locking members comprises mated rotatable and stationary members, said rotatable member having an aperture alignable with the passage of said tube, said flexible tension member passing freely through said aperture, said rotating member adapted to be rotated within said stationary member and thereby trap said flexible tension member between said rotatable and stationary members while still permitting liquid to flow in said passage, through said aperture.

9. The medical device of claim 8 wherein said rotatable member and said stationary member are of the general form of a stopcock.

10. A method of fixing a medical device within a body cavity comprising:

providing a medical device comprising an elongated member for insertion into the body, a flexible tension member extending along said elongated member to an attachment upon which tension is desired to be applied, and locking means associated with the elongated member at a point outside of the body to secure said flexible member under tension, said locking means comprising a pair of locking members disposed in close association with each other at a predetermined point along the proximal portion of said flexible tension member, one sid locking member being movable relative to the other said locking member in motion laterally across the path of said tension member under tension to a locking position in which the tension member is bent and secured between said cooperating locking members;

inserting said distal end of said elongated member into said body cavity, pulling the proximal end of said flexible tension member and thereby causing said distal end of said elongated member to form, within said body cavity, into a shape capable of resisting displacement from the body cavity, and moving one said locking member across the path of said flexible tension member to secure it.

11. The method of claim 10 comprising rotating one said locking member relative to the other, effectively jamming said flexible tension member therebetween.

12. The method of claim 10 or 11 wherein said elongated member is in the form of a catheter having proximal and distal ends and defining a conduit for flow of fluid therewithin, and said method comprises securing said flexible tension member in a manner still permitting flow of fluid from said distal end to said proximal end of said catheter, and attaching a conduit-forming member to said proximal end of said catheter whereby said flexible tension member is positioned within said conduit-forming member.

* * * * *

UNITED STATES PATENT AND TRADEMARK OFFICE
CERTIFICATE OF CORRECTION

PATENT NO. : 4,740,195
DATED : April 26, 1988
INVENTOR(S) : Andrew P. Lanciano

It is certified that error appears in the above-identified patent and that said Letters Patent are hereby corrected as shown below:

Col. 4, line 25, "TM" should be --$^{TM}$--;

Col. 8, line 8, "one sid" should be --one said--.

Under REFERENCES (Other Publications)

Gunther: "Smal-" should be --Small--.
"1-Looped" should be --Looped--.

Signed and Sealed this

Fifteenth Day of November, 1988

*Attest:*

DONALD J. QUIGG

*Attesting Officer*  *Commissioner of Patents and Trademarks*